United States Patent [19]

Maes

[11] 4,298,687

[45] Nov. 3, 1981

[54] PROCESS FOR THE DETERMINATION OF COMPOUNDS SHOWING AMONG THEMSELVES SPECIFIC BINDING AFFINITIES BY THE USE OF A SOLID PHASE

[76] Inventor: Roland Maes, 2, Ave. d'Alsace, 67 000 Strasburg, France

[21] Appl. No.: 85,438

[22] Filed: Oct. 16, 1979

[30] Foreign Application Priority Data

Oct. 31, 1978 [FR] France .................. 78131279

[51] Int. Cl.$^3$ ............................................. C12Q 1/66
[52] U.S. Cl. ........................................ 435/7; 23/230; 424/8; 424/12
[58] Field of Search ............... 435/7, 28; 23/230 B; 424/7, 8, 12, 13

[56] References Cited

U.S. PATENT DOCUMENTS

| | | | |
|---|---|---|---|
| 3,826,613 | 7/1974 | Parikh et al. | 435/7 X |
| 3,839,153 | 10/1974 | Schuurs et al. | 435/7 |
| 3,905,767 | 9/1975 | Morris et al. | 435/7 X |
| 4,011,308 | 3/1977 | Giaener | 435/7 X |
| 4,016,043 | 4/1977 | Schuurs et al. | 435/7 |
| 4,067,959 | 1/1978 | Bolz | 435/7 |
| 4,070,246 | 1/1978 | Kennedy et al. | 435/7 |
| 4,134,792 | 1/1979 | Boguslaski et al. | 435/7 X |

OTHER PUBLICATIONS

Leif Wide, Radioimmunoassays employing immunosorbents, Karolinska Symposium on Research Methods in Reproductive Endocrinology, pp. 207–221, 1969.
A. T. Jagendorf et al., Biochimica et Biophysics Acta, vol. 78, pp. 516–528, 1963.
R. G. C. Gallop et al., Biochem. J., vol. 101, pp. 711–716; 1966.
Rolf Axen et al., Nature, vol. 214, pp. 1302–1304, 1967.
Nakane and Pierce, Journal of Histochemistry and Cytochemistry, vol. 44, pp. 789–791, 1966.
Stratis Aurameas et al., Immunochemistry, vol. 6, pp. 53–66, 1969.
Tesser et al., FEBS Letters, vol. 23, No. 1, pp. 56–58, 1972.
N. Weliky et al., Immunochemistry, vol. 1, pp. 219–229, 1964.
Peter S. Ambrus et al., Journal of Medicine, vol. 6, Nos. 3 & 4, pp. 217–240, 1975.
Handbook of Experimental Immunology, Blackwell Scientific Publication, 2nd Ed., edited by D. M. Weir, pp. 17.1–17.18.
John K. Inman, Constant Linkage of Functional Groups, Ligands and Proteins to Polyacrylamide Beads, p. 58.
Jerker Porath et al., Nature, vol. 215, pp. 1491–1492, 1967.
Kenin Catt et al., Science, vol. 158, pp. 1570–1572, 1967.
Eva Engvall et al., The Journal of Immunology, vol. 109, No. 1, pp. 129–135, 1972.
Warren J. Dillman et al., Journal of Colloid and Interface Science, vol. 44, No. 2, pp. 221–241, 1973.

*Primary Examiner*—Robert J. Warden
*Attorney, Agent, or Firm*—Mason, Fenwick & Lawrence

[57] ABSTRACT

Process for the determination of substances having specific binding affinities, in which the substance to be determined is subjected to a specific binding reaction with a primary binding partner present in limited and known amount. That part of the primary binding partner that remains unreacted and free in solution after completion of the specific binding reaction is specifically absorbed on a solid phase consisting in a polyacrylamide gel sensitized by a compound endowed with specific binding properties for the primary binding partner, and the thus absorbed primary binding partner is then detected, as by an enzymatic or fluorescent reaction.

9 Claims, No Drawings

PROCESS FOR THE DETERMINATION OF COMPOUNDS SHOWING AMONG THEMSELVES SPECIFIC BINDING AFFINITIES BY THE USE OF A SOLID PHASE

This invention relates an improved process for the determination of antigens and their respective antibodies or substances endowed with haptens and also of substances showing between themselves a known specific binding affinity. The process improved is of the type using a solid phase sensitised by one of the elements which intervene in the specific affinity between such substances.

Processes are already known that exploit the specific binding affinity that may exist between two substances. These processes are based on the following principle: a binding reaction of specific affinity is established between a substance in solution and its binding partner attached to a solid phase. The solid phase is constituted of a gel of agarose, of cellulose grains, of latex or else a surface of polystyrene. Once the reaction has taken place, the solid phase is isolated and the quantity of the substance to be determined which is specifically bound to the solid phase by a binding reaction of specific affinity, is measured either through the agency of an enzyme covalently linked to one of the constituents of the system or through a third reactive component covalently linked to an enzyme reagent which is specifically binding for one of the constituents of the system of detection. The marker in use is generally an enzyme but it may be also another element of detection such as Iodine$^{125}$ or Iodine$^{131}$, tritium or a fluorescent material such as isothiocyanate.

The sensitivity of systems for detecting substances which are present in unknown quantity in a liquid, based on the binding of this substance in a specific way to a binding partner attached to a solid phase, is in general poor, especially when an enzyme marker is used. This reduced sensitivity is primarily due to the fact that the reagents used are not physico-chemically inert. They react among themselves in unspecific ways and these unwanted reactions considerably increase the "background noise" of the specific binding reaction analysed.

Also, the solid phase usually adsorbs in an unspecific and variable way the majority of the substances with which it enters in contact. Solid phases for example readily adsorb the gamma-globulins which are very frequently used in these tests of detection.

On the other hand, substances possessing specific binding affinities, which are covalently linked to solid phases composed of polymers of carbohydrates, such as cellulose, sephadex and agarose, are slowly released in the surrounding medium in the course of time. The solid phase loses gradually the sensitising element, with a loss of sensitivity (G. I. Tesser et al. FEBS letters, 13, 56, 1972).

Finally, where the marker is an enzyme, a colored substance is produced by the final enzymatic reaction and tends to precipitate on the activated solid phase.

The choice and preparation of the reagents used, and more specifically the choice of the solid phase and its process of activation, are essential for the formulation of a detection system based on the use of a solid phase which will be specific, sensitive and really useful and reliable in the daily practise of the analyses performed by diagnostic laboratories.

The object of the present invention is such a process.

Generally, the determination of a substance by tests using a solid phase, is realised by direct measurement of the amount of the unknown substance that is absorbed on the solid phase sensitised by a binding partner specific for this substance. The present invention applies an indirect approach, i.e. measures the amount of the binding partner that remains free after completion of the specific binding reaction with the substance to be determined. The binding partner, initially present in solution in a known and limited quantity, of which part subsists free in solution after completion of the specific binding reaction with the substance to be determined, is thereafter specifically absorbed on a solid phase consisting of a gel of polyacrylamide activated by a dialdehyde or a trioxane or paraldehyde, which has been sensitised by a substance endowed with specific binding properties for the primary binding partner. The sensitisation of the gel may be accomplished by an antibody against the primary binding partner or else by a substance of the same nature as the substance to be determined.

The important point is that the remainder or residue of the binding partner subsisting free in solution after the first specific affinity reaction, be absorbed totally and specifically on the solid phase and that nothing else be absorbed.

The solid sensitised phase must be essentially inert. It is another object of this invention that the polyacrylamide gel sensitised after activation by a dialdehyde or a trioxane or paraldehyde, is to a large extent deactivated, if need be, so as to restore its physico-chemical inertness, as necessary to reduce to a negligible amount all undue unspecific absorptions.

A process of detection in accordance with the invention and applicable to all haptens and antigens, and to all substances possessing specific binding partners and whose sensitivity is satisfactory, consists in general of the following steps:

1. 50 µl to 1 ml of a physiological fluid or a buffer containing the substance to be determined is brought to a pH adequate for the establishment of a specific binding reaction with its binding partner. This is done by the addition of a small amount of buffer, the pH being usually set between 5 and 9, preferably 8.

2. The solution is mixed with a volume of buffer (e.g. 0,4 ml) containing usually 1% bovine serum albumin and 0.85% sodium chloride at pH 8.0 and containing also a known and limited amount of its binding partner.

The primary affinity binding reaction takes place in solution during the time and at the temperature necessary to achieve the completion of the reaction. For rapid determinations, 30 minutes at room temperature are sufficient. To achieve a high sensitivity, 3 hours at 37° C. or else 24 hours at R.T. are applied.

Measurement of the quantity of this primary binding partner that remains free in solution after the primary specific binding reaction is carried out, which makes possible a the determination of the quantity of binding substance present, by the construction of a standard curve.

3. After achievement of the primary binding reaction of specific affinity in solution, the solution is supplemented by a polyacrylamide gel sensitised by a substance that is specifically binding for the primary binding partner. One ml of a 3% gel suspension (V/V), or the sediment thereof, is added to the solution. The solid phase is added in excess, so as to specifically bind all the free-remaining primary binding partner. The determination of the concentration, in a solution, of certain substances such as antibodies, specific or not, may also be effected by this operation of fixation on a sensitised polyacrylamide solid phase. The process of absorption of the remainder of the primary binding partner on the solid phase is completed preferentially during 18 to 24 h at R.T., but may be substantially reduced (e.g. to 2 hours) if only a low sensitivity is required.

4. The solid phase is therefter isolated, for example through a short spin-down at 2.000 rpm during 30" and washed once with cold tap water.

5. After washing, the quantity of the primary binding partner attached in a specific manner on the solid phase is revealed by a second reaction of specific binding. One may for this purpose use any substance endowed with a specific binding affinity for this primary binding partner. Usually one uses an antibody.

The revelator-antibody, present in excess in 1 ml of a buffer solution, usually containing albumin and sodium chloride and brought to pH 8.0, is labeled by an enzyme (peroxidase, alkaline phosphatase, lysozyme, malate dehydrogenase, beta-galactosidase, catalase, etc. . . . ) or by a radio-element ($H^3$, $I^{125}$, $I^{131}$) or even a fluorophore such as dansyl-chloride, N- (7-dimethylamino-4-methyl-oxo-chromenyl)maleimide (DACM), fluorescein isothiocyanate, and dichloro-triazinyl-aminofluorescein (DTAF).

6. After completion of this secondary specific binding reaction, which takes place preferentially during 6 to 7 hours at R.T. if a high sensitivity is aimed at but which may be shortened to 2 hours or less if a low sensitivity is desired, the solid phase is isolated, for example by centrifugation, and the solid phase is washed once with cold tap water. The quantity of the labeled enzyme fixed on the solid phase is thereafter analyzed by passage of the solid phase through a radioactivity counter, by measurement of the fluorescence or by an enzymatic reaction.

All the steps of the determination which take place in a heterogeneous system composed of a solid phase in suspension in a liquid, are conducted under constant agitation.

Non specific binding reactions may occur when a solid phase is suspended in a liquid (Engvall and Perlmann: Enzyme-linked immunosorbent ELISA III. J. Immunol. 109, 129, 1972). The components of the detection system described herein, of which the physico-chemical inertness is important for satisfactory results, are in the first place the product of linkage of a specific binding partner with a fluorophore or an enzyme. We use to this effect substances purified by immuno-absorption, according to known procedures (Use of antibody bound to modified cellulose as an immuno-specific absorbent of antigens. A. Jugendorf et. al. B.B.A. 78, 516–528, 1963). Once purified by affinity chromatography, the substance is linked to an enzyme. The product of the linkage of a protein or other substance to an enzyme which is achieved by the help of a bridging agent such as glutaraldehyde or chloroformiate, is unsatisfactory because the yield is poor, because the coupling results in aggregates, and because these aggregates absorb to a high degree unspecifically to solid phases. An acceptable linking consists in a controlled peroxylation of the carbohydrates present in an enzyme, with formation of a Schiff-base between the aldehydes formed and the $NH_2$-terminals of the substance to be linked. The Schiff-base formed is thereafter strenghtened by treatment with a borohydride or cyanoborohydride reducing agent such as K-borohydride or Na-cyanoborohydride (Nakane and Pierce, J. Histochem. Cytochem. 14, 929, 1966).

The second reagent where inertness is important is the activated and sensitised solid phase.

The physico-chemical inertness of polyacrylamide gel is satisfactory. A system of activation of the gel that maintains to a large extent this original inertness consists in a treatment of the wet gel by paraldehyde, trioxane or a dialdehyde such as glutaraldehyde. The activation takes place during 18 hours at a temperature comprised between RT and 90° C., preferably 60° C., in a solution of mineral salts 0.01 to 1 molar, preferably 0.1 M, at a pH comprised between 3 and 9, preferably 8.

The concentration of the bridging agent ranges from 0.2% to 20%, preferably 5% and that of the polyacrylamide gel is comprised between 1% and saturation, preferably 10% (V/V, the gel being wet).

After activation, the gel is repeatedly decanted in water to eliminate the fines and thereafter in a buffer composed of mineral salts at a pH comprised between 5 and 10, preferably 7.5 The gel is filtered and sensitised by the sensitising agent in solution in a buffer of pH comprised between 5 and 10, preferably pH 7.5. The preferred process is to add to the wet cake obtained after filtration, a quantity of buffer at pH 7.5 containing the sensitising agent, which is sufficient to just cover the wet cake by a film of liquid. The concentration of the sensitising substance is variable. Typically, 50 grams of dry polyacrylamide gel correspond to 140 gr of the gel in a wet cake, and the whole of this amount is sensitised by 10 mg of a highly purified human gonadotrophic hormone. The sensitisation may proceed at 4° C., RT or 37° C. during 24 hours to 48 hours. After sensitisation, the gel is repeatedly washed in distilled water and buffers of various ionic strenghts (up to 2 M Nacl) and various pH's (4 to 8.5).

The activation of the polyacrylamide gel introduces charged groups in the gel. The physico-chemical inertness of the gel is restored by treatment with chemical agents carrying —$NH_2$ groups. The agents most effective for this purpose are hydroxylamine, acrylamide, glutamine, acetamide and formamide. The saturation of the free aldehyde functions originating from the activation is done by treating the gel at 10% (V/V) in a solution of mineral salts 0.1 M to 1 M at a pH preferentially 8.0, by a concentration in —$NH_2$containing agents varying from 0.0001 M to 0.1 M, preferably 0.01 M.

The time allowed for the reaction lasts in general 24 hours at RT and may extend for 48 hours at a temperature between 20°–37° C. After saturation of the aldehydic functions by an $NH_2$ carrying agent, the gel is washed repeatedly in water and buffer and suspended at 10% in a conservating medium.

EXAMPLE 1

Determination of HCG 0.4 ml of a buffer solution containing 400 ng of rabbit anti HCG antibody of the IgG type are mixed with 50 $\mu$l of a buffer solution containing known amounts of HCG ranging from 1.25 to 320 m IU/ml. Incubation took place at RT for 24 h. The solution was thereafter supplemented with 1 ml of a 3% polyacrylamide gel sensitised with HCG and saturated with glutamine. Incubation lasted overnight (18 h) at RT under constant agitation.

The gel was washed once with 1 ml cold tap water and further incubated during 7 h at RT under constant agitation, in the presence of 1 ml of 1:2000 concentration of peroxydase-labeled sheep antiglobulines against rabbit IgG.

After washing with 1 ml of cold tap water, the presence of peroxydase fixed on the solid phase was revealed by incubation of the gel under constant agitation at RT in 1 ml of a solution of a phenylene-diamine at 0.1% in 0.2 M citrate buffer at pH 5.0, containing 1 µl/ml of $H_2O_2$ (30 volumes). After 50' incubation, the enzymatic reaction, yielding a yellow color, was stopped by 100 µl $H_2SO_4$ 9 M. The solid phase was eliminated by centrifugation and the absorbance of the supernatant was read at $A_{480}$. The limit of sensitivity of the method applied was, in this case, 2.5 m IU HCG/ml.

EXAMPLE II

Determination of equine LH by a heterologous immunologic reaction 0.1 ml of a solution containing 50 µg/ml of rabbit antibody against sheep LH was reacted with 1 ml of a gel suspension at 3% of polyacrylamide in a buffer at pH 8.0 containing 1% bovine albumin. The gel was sensitised with mare PLH and saturated with glutamine. After incubation under constant agitation at RT during 18 hours, the gel was isolated, washed as described in example 1 and incubated during 7 hours at RT with a 1:2000 solution of peroxydase-labeled goat anti-globulines against rabbit IgG. After washing with cold tap water, the presence of an enzymatic activity fixed on the gel was detected, as described in example 1. The absorbance $A_{480}$ measured was 0.7.

The base-line of the detecting system being so established, the detection of PLH was done as follows: 0.1 ml of rabbit antibodies against sheep LH (50 µg/ml) was incubated with 0.1 ml of a solution containing 20 m IU/ml equine LH, during 3 h at 37° C. and followed by absorption of the free-remaining antibodies on a sensitised solid phase, as described. This resulted in a drop of absorbance of 15% compared to the control. Such a 15% drop is considered as the limit of sensitivity of the system.

EXAMPLE III

Determination of oestradiol

Oestradiol-6-(-O-carboxymethyloxyme) was conjugated to ovalbumin according to a known process (Erlanger, B.F. et al. in: Methods in Immunology and Immunochemistry, Williams and Chase, Ed. Vol. I. pp 144–151 Academic Press New York) and the conjugate was used to sensitise a polyacrylamide gel, thereafter saturated with glutamine.

Anti-oestradiol antibodies are commercially available (Sigma, St Louis, Mo., 63178) After reaction at 37° C. during 3 hours between known amounts of oestradiol and the antibodies solubilised in 1 ml of a buffer at pH 8.0 containing 1% bovine albumin, the free remaining antibody was absorbed on a solid phase as described in examples 1 and II. The revelation of the peroxydasic activity localised on the solid phase was achieved by incubation of the gel under constant agitation in 1 ml homovallinic acid (0.25%) in a Tris-HCl buffer (0.1 M) at pH 8.0, containing 0.005% $H_2O_2$. After incubation during 60 minutes at RT, the solid phase was eliminated through centrifugation. The intensity of the fluorescence in the supernate was measured at 320 nm (excitation) and 420 nm (emission). The results of this analysis showed that oestradiol is determined, by the process described, between 50 pg and 1 ng per tube.

EXAMPLE IV

Qualitative and quantitative determination of human antiglobulines

A polyacrylamide gel activated by paraldehyde was sensitised with equine gamma-globulines and thereafter saturated with acrylamide. One ml of a gel suspension at 5% (V/V) was centrifugated and the sediment incubated in the presence of 0.15 ml of human serum originating from a rheumatoid-arthritic patient, diluted to 1 ml by a buffer-albumin at pH 8.0, as described in examples 1 and II.

After incubation during 3.5 h at 37° C., the gel was isolated and washed, as described in examples 1 and II. The nature of the human antiglobulins fixed on the gel through a specific affinity binding to the equine gamma-globulins was established by incubation of the solid phase in 1 ml of a solution of rabbit IgG antibodies against human IgG or human IgM. These antibodies are commercially available and may be purified according to well-established methods.

After incubation during 6 h at RT in the presence of these rabbit antibodies specific for human IgG or IgM globulins, the gel is isolated, washed and incubated during 7 h in the presence of 1 ml peroxydase-labelled goat anti-rabbit antibodies. Determination of the enzymatic activity fixed on the solid phase proceded as described in example 1. The presence of human antiglobulins results in an increased intensity of coloration.

Quantification of the detection process requires the elaboration of two standard curves which will accurately determine the quantity of human anti-IgG or human anti-IgM rabbit gammaglobulins specifically bound on the gels, since this quantity reflects the quantity of human antiglobulins specifically attached to equine gammaglobulins and determines the quantity of peroxydase-labelled goat antibodies against rabbit IgG that will be attached to the gel in the final immunological step.

To this end, a polyacrylamide gel is sensitised by human gammaglobulins of the IgG and IgM types. Various concentrations of known amounts of monospecific rabbit gammaglobulins, affinity purified, are analysed by the aid of these sensitised gels in an experimental protocol identical to the one where the sensitised agent of the gel was equine gammaglobulins. This will allow the construction of the two reference curves necessary for a quantitative determination.

The application of the process described, in accordance with the discovery, allowed the detection of 10 ng/ml serum of human IgG antiglobulins and 2 ng/ml serum of human IgM antiglobulins.

I claim:

1. A process for the determination of compounds having specific binding affinities by the steps comprising adding to a solution containing the compound to be determined, a soluble primary binding partner capable of specific binding affinity with such compound and in a predetermined amount exceeding the quantity of the compound to be determined, whereby excess primary binding partner remains free in solution after completion of the specific binding reaction; specifically adsorbing such excess specific binding partner in a solid phase consisting of a polyacrylamide gel which has been activated by a dialdehyde, a trioxane, or paraldehyde and then sensitized by a compound having specific binding affinity for the primary binding partner, the amount of said sensitized solid phase being sufficient to adsorb thereon all of said excess primary binding partner; deactivating the thus-sensitized solid phase with a deactivating compound carrying $NH_2$ groups, chosen among the group consisting of hydroxylamine, acrylamide, glutamine, acetamide and formamide and then revealing the extent of said adsorption of said excess primary binding partner on said sensitized solid phase by reacting the adsorbed primary binding partner with a labeled binding partner having specific binding affinity for said primary binding partner and measuring the amount of reacted labeled binding partner.

2. The process according to claim 1 wherein said adsorbed excess binding partner is revealed by reaction with an antiglobulin having specific binding affinity for said primary binding partner and which is labeled with an enzyme, a radioactive element, or a fluorophore for purposes of said measurement.

3. A process according to claim 2 wherein said labeling is carried out by coupling said antiglobulin after purification by affinity chromatography with a fluorophore or an enzyme, said coupling being effected through peroxydation of carbohydrates present in the enzyme or in said sensitizing compound, and then subjecting the coupling product to chemical reduction with borohydride or cyanoborohydride.

4. The process of claim 1 wherein said activated polyacrylamide gel is sensitized by the compound to be determined or by an antibody having specific binding affinity for the primary binding partner.

5. The process of claim 1 wherein said labeled binding partner used for revealing the adsorption of the excess primary binding partner is a labeled antibody having specific binding affinity for said primary binding partner.

6. A process according to claim 1 wherein said sensitized solid phase is deactivated by saturating the same with said deactivating compound.

7. A process for the quantitative determination of compounds having specific binding affinities by the steps comprising adding to a solution containing an unknown amount of the compound to be determined, a solid phase consisting of a polyacrylamide which is activated by a dialdehyde, a trioxane, or paraldehyde and then sensitized by a compound having specific binding affinity for the unknown compound, the amount of said sensitized solid phase being sufficient to adsorb thereon all of said unknown compound; deactivating the thus-sensitized solid phase with a deactivating compound carrying $NH_2$ groups, chosen among the group consisting of hydroxylamine, acrylamide, glutamine, acetamide and formamide; and then revealing the extent of said adsorption of said unknown compound on said sensitized solid phase by reacting the adsorbed unknown compound with a labeled binding partner having specific binding affinity for said unknown compound and measuring the amount of reacted labeled binding partner.

8. The process of claim 7 wherein the labeled binding partner reacted with the adsorbed unknown compound to reveal the extent of its adsorption is a labeled antibody having specific binding affinity for said adsorbed unknown compound.

9. The process of claim 8 wherein said labeled antibody is an antiglobulin having specific binding affinity for said adsorbed unknown compound and which is labeled with an enzyme, a radioactive element, or a fluorophore for purposes of said measurement.

* * * * *